United States Patent
Koseoglu et al.

(10) Patent No.: US 11,326,108 B1
(45) Date of Patent: May 10, 2022

(54) INTEGRATED PROCESS FOR THE PRODUCTION OF ISONONANOL AND STABLE / LUBRICATING ALCOHOL GASOLINE BLENDING COMPONENTS

(71) Applicant: Saudi Arabian Oil Company, Dhahran (SA)

(72) Inventors: Omer Refa Koseoglu, Dhahran (SA); Sohel Shaikh, Dhahran (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/198,705

(22) Filed: Mar. 11, 2021

Related U.S. Application Data

(63) Continuation of application No. 17/196,314, filed on Mar. 9, 2021.

(51) Int. Cl.
  *C10G 9/36*  (2006.01)
  *C10G 45/38* (2006.01)
  *C10G 27/04* (2006.01)

(52) U.S. Cl.
  CPC .............. *C10G 9/36* (2013.01); *C10G 27/04* (2013.01); *C10G 45/38* (2013.01); *C10G 2300/1092* (2013.01); *C10G 2400/02* (2013.01); *C10G 2400/04* (2013.01)

(58) Field of Classification Search
  CPC .......... C10G 9/36; C10G 27/04; C10G 45/38; C10G 2300/1092; C10G 2400/02; C10G 2400/04
  See application file for complete search history.

(56) References Cited

U.S. PATENT DOCUMENTS

| | | | |
|---|---|---|---|
| 5,864,052 A | 1/1999 | Nierlich et al. | |
| 5,912,191 A | 6/1999 | Nierlich et al. | |
| 6,153,851 A | 11/2000 | Schneider et al. | |
| 6,403,840 B1 | 6/2002 | Zhou et al. | |

(Continued)

FOREIGN PATENT DOCUMENTS

WO  2017146876 A1  8/2017

OTHER PUBLICATIONS

Notice of Allowance and Fee(s) Due dated Dec. 14, 2021 pertaining to U.S. Appl. No. 17/198,735, filed Mar. 11, 2021, 14 pages.

*Primary Examiner* — Thuan D Dang
(74) *Attorney, Agent, or Firm* — Dinsmore & Shohl LLP

(57) ABSTRACT

In accordance with one or more embodiments of the present disclosure, a method for producing alcohol gasoline blending components includes cracking, in a steam cracker, a hydrocarbon feed to form a first ethylene stream, a first propylene stream, and a $C_4$ stream comprising isobutene and butadiene; reacting, in a methyl tertiary butyl ether (MTBE) unit, the $C_4$ stream with a methanol stream to form MTBE and a butadiene-rich $C_4$ stream; selectively hydrogenating, in a butadiene unit, the butadiene-rich $C_4$ stream to form a butene-rich $C_4$ stream including butene-1, cis-butene-2, and trans-butene-2; producing, in an isononanol unit, isononanol and an olefin-rich stream from the butene-rich $C_4$ stream; and hydrating the olefin-rich stream in a hydration unit by combining the olefin-rich stream with a water stream and a catalyst composition to produce the alcohol gasoline blending components.

15 Claims, 2 Drawing Sheets

(56) References Cited

U.S. PATENT DOCUMENTS

| | | |
|---|---|---|
| 6,447,558 B1 | 9/2002 | Yeh et al. |
| 7,437,812 B2 | 10/2008 | Baird |
| 9,834,497 B2 | 12/2017 | Shaikh et al. |
| 9,914,681 B2 | 3/2018 | Geilen et al. |
| 10,059,645 B2 | 8/2018 | Shaikh et al. |
| 10,214,466 B2 | 2/2019 | Shaikh et al. |
| 2007/0135665 A1 | 6/2007 | Wiese et al. |
| 2009/0312583 A1 | 12/2009 | Sigl et al. |
| 2010/0048959 A1 | 2/2010 | Sigl et al. |
| 2015/0191410 A1 | 7/2015 | Frey et al. |
| 2018/0072647 A1 | 3/2018 | Stochniol et al. |

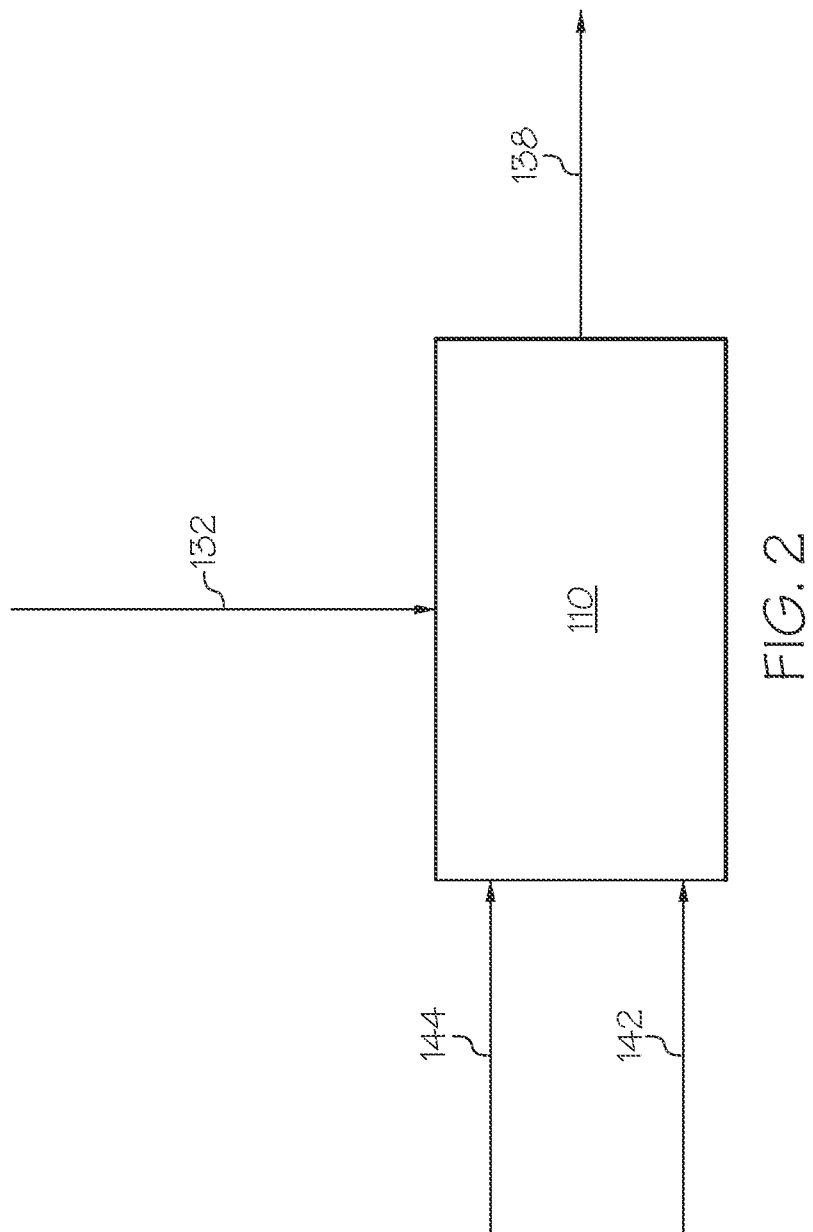

US 11,326,108 B1

INTEGRATED PROCESS FOR THE PRODUCTION OF ISONONANOL AND STABLE / LUBRICATING ALCOHOL GASOLINE BLENDING COMPONENTS

CROSS-REFERENCE TO RELATED APPLICATION

This application is a continuation of U.S. patent application Ser. No. 17/196,314, filed Mar. 9, 2021, which is incorporated by reference in its entirety in this application.

TECHNICAL FIELD

Embodiments of the present disclosure generally relate to petroleum products, and pertain particularly to a method for producing isononanol, gasoline blending components, and diesel blending components.

BACKGROUND

Steam cracking is a petrochemical process in which components of a hydrocarbon feedstock (e.g., hydrogen rich paraffinic and naphthenic hydrocarbons) are converted into light olefins, such as ethylene, propylene and butenes.

Oxo technology is a leading technology for the manufacture of oxo alcohols from olefins. This technology includes oxo alcohol production processes in which alcohols are produced at low pressure over homogeneous catalysts (e.g., rhodium) via hydroformylation reactions of an olefin with syngas (CO and $H_2$), followed by hydrogenation reactions of an intermediate aldehyde. For example, propylene can be hydroformylated to produce butyraldehyde and iso-butyraldehyde, which are then hydrogenated to produce normal butanol and iso-butanol respectively. The production of 2-ethylhexanol, for example, is achieved by aldolization of the normal-butyraldehyde followed by hydrogenation of the aldol intermediates. Isononanol, which is used commercially in the production of certain plasticizers, may be produced by this process, but an olefin-rich stream byproduct is produced along with the isononanol.

SUMMARY

There is, therefore, a continual need for novel methods for increased isononanol yield and converting low value byproducts of isononanol synthesis into high value gasoline and diesel blending components. Embodiments of the present disclosure are directed to such methods.

According to one embodiment, a method for producing alcohol gasoline blending components includes cracking, in a steam cracker, a hydrocarbon feed to form a first ethylene stream, a first propylene stream, and a $C_4$ stream comprising isobutene and butadiene; reacting, in a methyl tertiary butyl ether (MTBE) unit, the $C_4$ stream with a methanol stream to form MTBE and a butadiene-rich $C_4$ stream; selectively hydrogenating, in a butadiene unit, the butadiene-rich $C_4$ stream to form a butene-rich $C_4$ stream including butene-1, cis-butene-2, and trans-butene-2; producing, in an isononanol unit, isononanol and an olefin-rich stream from the butene-rich $C_4$ stream; and hydrating the olefin-rich stream in a hydration unit by combining the olefin-rich stream with a water stream and a catalyst composition to produce the alcohol gasoline blending components.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which:

FIG. 2 is a process flow diagram in accordance with embodiments described herein.

DETAILED DESCRIPTION

Figure 1:
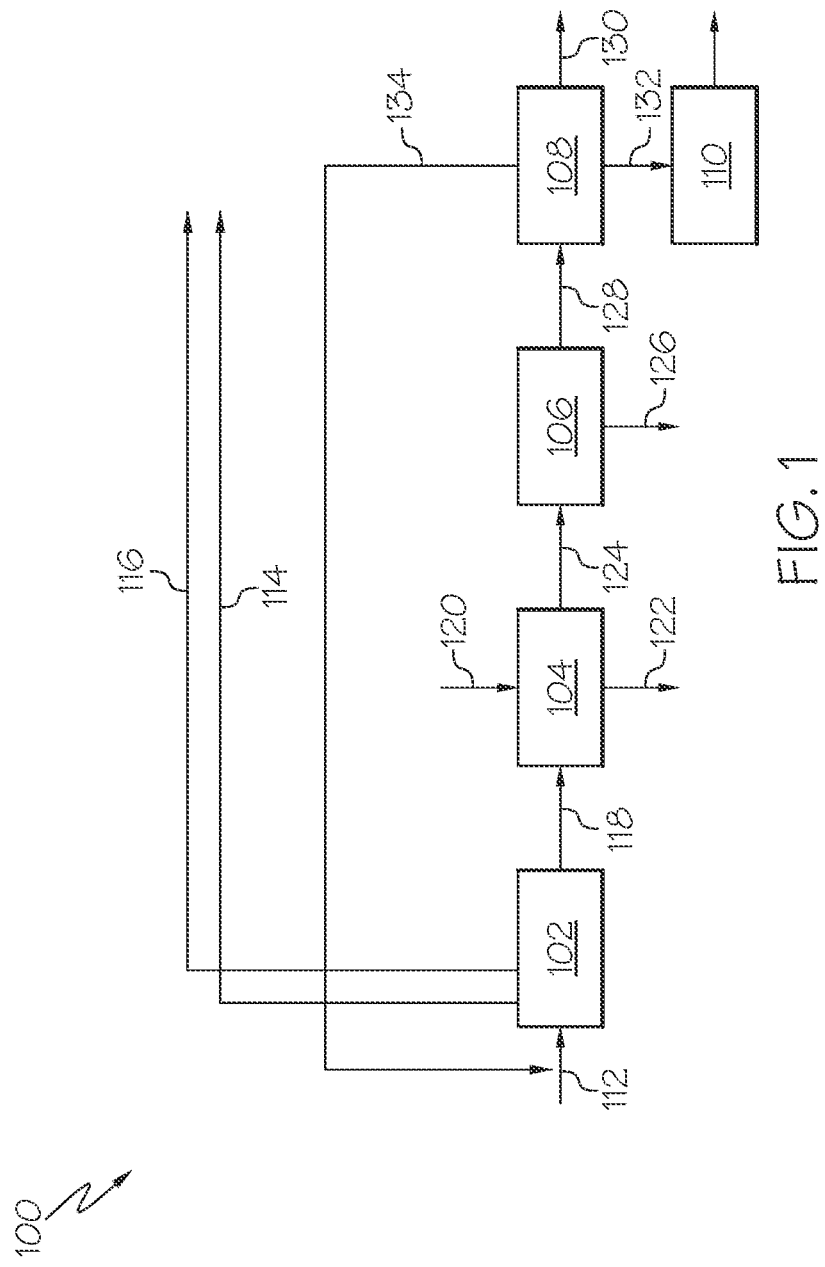
FIG. 1 is a process flow diagram in accordance with embodiments described herein.

Embodiments described herein relate to novel methods for increased isononanol yield and converting low value byproducts of isononanol synthesis into high value gasoline and diesel blending components.

As used herein, the term "hydrocarbon oil" or "hydrocarbon feedstock" or "hydrocarbon feed" refers to an oily liquid composed mostly of a mixture of hydrocarbon compounds. Hydrocarbon oil may include refined oil obtained from crude oil, hydrocarbon mixtures boiling in a range of 350° C. to 750° C., synthetic crude oil, hydrocarbon mixtures containing 1000 parts per million by weight ("ppmw") $C_5$-asphaltenes, bitumen, oil sand, shale oil, or coal oil. The term "refined oil" includes, but is not limited to, vacuum gas oil (VGO), deasphalted oil (DAO) obtained from a solvent deasphalting process, demetallized oil (DMO), light and/or heavy coker gas oil obtained from a coker process, cycle oil obtained from an FCC process, and gas oil obtained from a visbreaking process.

As used herein, the term "hydrocarbon" refers to a chemical compound composed entirely of carbon and hydrogen atoms. An expression such as "$C_x$-$C_y$ hydrocarbon" refers to a hydrocarbon having from x to y carbon atoms. For instance, a $C_1$-$C_5$ hydrocarbon includes methane, ethane, propane, the butanes, and the pentanes.

As used herein, the term "conduit" includes casings, liners, pipes, tubes, coiled tubing, and mechanical structures with interior voids.

As used herein, the term "hydrogen/oil ratio" or "hydrogen-to-oil ratio" or "hydrogen-to-hydrocarbon ratio" refers to a standard measure of the volume rate of hydrogen circulating through the reactor with respect to the volume of feed. The hydrogen/oil ratio may be determined by comparing the flow volume of the hydrogen gas stream and the flow volume of the hydrocarbon feed.

As used herein, the term "liquid hourly space velocity" or "LHSV" refers to the ratio of the liquid flow rate to the catalyst volume.

As used herein, the term "gas hourly space velocity" or "GHSV" refers to the ratio of the gas flow rate of a gas phase reagent to the catalyst volume.

As used herein, the term "weight hourly space velocity" or "WHSV" refers to the ratio of the weight of reagent flow to the catalyst weight.

As used herein, the term "research octane number" or "RON" refers to a property of fuels that is related to the amount of compression the fuel can withstand before detonating. RON may be calculated similar to the method found in Anderson et al., "Calculations of the Research Octane and Motor Gasolines from Gas Chromatographic Data and a New Approach to Motor Gasoline Quality Control," *Journal of the Institute of Petroleum*, vol. 52, pp. 83-93 (1972). In the method, each compound has an index, and the individual components are grouped. The octane number is calculated from the octane number of the group. The concentration of each group is multiplied with the octane number of each component and the sum gives the predicted octane number. In addition, the standard ASTM D2699, "Standard Test Method for Research Octane Number of Spark-Ignition Engine Fuel," may be used to determine the RON.

As used herein, the terms "cetane number," "CN," "cetane index," or "CI" refer to a property of diesel fuels inversely related to the diesel fuel's ignition delay, i.e., the time period between the start of ignition and the first identifiable pressure increase during combustion of the fuel. CN may be obtained in accordance with ASTM D613, which uses a cetane engine to determine the CN, or ASTM D976 or D4737, each of which uses the density and boiling point properties of the diesel fuel to calculate the CN.

As used herein, the term "decreased content" of a substance means that a concentration of the substance is greater before passing through a stage of the process under examination than it is after passing through the stage. As used herein, the term "increased content" of a substance means that a concentration of the substance is greater after passing through a stage of the process under examination than it is before passing through the stage.

As used herein, any stream that is referred to as "rich" in some chemical species contains 50% or more by volume of that chemical species.

In the description of the embodiments that follows, like numerals denote like components across the various figures.

In accordance with one or more embodiments, the present application discloses systems and methods for producing isononanol and gasoline and diesel blending components. In one or more embodiments, the system includes a steam cracker for cracking a hydrocarbon feed to form an ethylene stream, a propylene stream, and a $C_4$ stream that comprises isobutene and butadiene. The system also includes a methyl tertiary butyl ether (MTBE) unit fluidly connected to the steam cracker. In the MTBE unit, the isobutene in the $C_4$ stream reacts with a methanol stream to form MTBE and a butadiene-rich $C_4$ stream.

The system further comprises a butadiene unit fluidly connected to the MTBE unit. In the butadiene unit, the butadiene-rich $C_4$ stream is further reacted to form a butene-rich $C_4$ stream. The butene-rich $C_4$ stream is then transferred to an isononanol unit, where a portion of the butene-rich $C_4$ stream undergoes a series of reactions to produce a $C_8$, $C_{12}$, and $C_{16}$ olefin-rich stream and an isononanol stream. The olefin-rich stream undergoes oxidation in an oxidation unit to produce epoxide gasoline blending components, hydration in a hydration unit to produce alcohol gasoline blending components, or hydrogenation in a hydrogenation unit to produce paraffins.

These and other aspects of the present methods are described in further detail below with reference to the accompanying figures, in which one or more illustrated embodiments and/or arrangements of the systems and methods are shown. The systems and methods of the present application are not limited in any way to the illustrated embodiments and/or arrangements. It should be understood that the systems and methods as shown in the accompanying figures are merely exemplary of the systems and methods of the present application, which can be embodied in various forms as appreciated by one skilled in the art. Therefore, it is to be understood that any structural and functional details disclosed herein are not to be interpreted as limiting the present systems and methods, but rather are provided as a representative embodiment and/or arrangement for teaching one skilled in the art one or more ways to implement the present systems and methods.

FIG. 1 provides an exemplary process flow diagram of embodiments described herein illustrating an integrated system 100 for producing isononanol and gasoline and diesel blending components. System 100 includes a steam cracker 102, an MTBE unit 104, a butadiene extraction unit 106, an isononanol unit 108, and a further processing unit 110. It should be understood that the steam cracker 102 and the other units of the system 100 are fluidly connected to one another via a series of conduits or lines as shown in FIG. 1. The steam cracker 102 is configured to receive a hydrocarbon feed via conduit 112. In embodiments, the hydrocarbon feed for the steam cracker 102 includes one or more hydrocarbons, such as ethane, propane, butane, liquefied petroleum gas (LPG), and naphtha. The hydrocarbon feed undergoes cracking reactions in the steam cracker 102 in the presence of steam. The cracking reactions of the hydrocarbon feed generally take place in pyrolysis tubes of the steam cracker 102. In one or more embodiments, the cracking reactions takes place at high temperatures from 800° C. to 900° C. In one or more embodiments, the residence time of the hydrocarbon feed in the steam cracker 102 is 0.1-2.0 seconds.

The resulting products of the cracking reaction may be controlled using several factors, including the hydrocarbon feedstock composition, the hydrocarbon-to-steam ratio, the cracking temperature and pressure, and the furnace residence time. In one or more embodiments, as shown in FIG. 1, the products of the cracking reaction in the steam cracker 102 are ethylene, propylene and a mixed $C_4$ stream that can comprise butenes (e.g., isobutene, butene-1, butene-2), butanes (e.g., n-butanes, isobutane), butadiene, and pyrolysis gasoline and fuel oil. In one or more embodiments, the ethylene, propylene, and mixed $C_4$ streams can exit the steam cracker separately. For example, as shown in FIG. 1, the ethylene stream can exit the steam cracker 102 via conduit 114, the propylene stream can exit the steam cracker 102 via conduit 116, and the mixed $C_4$ stream can exit the steam cracker 102 via conduit 118. Although not shown in FIG. 1, other products of the cracking reaction are also possible, including but not limited to, paraffinic gases such as methane and ethane, liquid products such as gasoline, and even heavier hydrocarbons such as pyrolysis fuel oil.

In one or more embodiments the steam cracker 102 comprises multiple stages, including a cracking furnace for the primary cracking reactions. In one or more embodiments, the steam cracker 102 includes one or more other stages such as a quench, a downstream compression stage, a cold box, and a recovery and purification stage. The recovery and purification stage can include one or more of a demethanizer, a deethanizer, a depropanizer, and a debutanizer for separating the ethylene, propylene, and mixed $C_4$ streams from one another before exiting the steam cracker 102 via separate conduits.

The mixed $C_4$ stream that exits the steam cracker 102 via conduit 118 is then fed to the MTBE unit 104. The MTBE unit 104 is also configured to receive a methanol stream via conduit 120. In the MTBE unit 104, the isobutene (isobutylene) in the mixed $C_4$ stream reacts with the methanol stream to form MTBE. The reaction of isobutene with methanol is provided as reaction scheme (1).

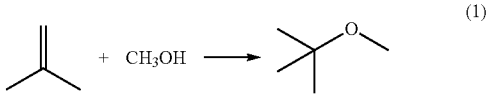

(1)

The remaining portion of the mixed C$_4$ stream that does not react with the methanol stream is a butadiene-rich C$_4$ stream as a result of the reactions. In one or more embodiments, the produced MTBE and the butadiene-rich C$_4$ stream can be separated into separate streams via a series of columns in the MTBE unit 104. Additionally, the series of columns in the MTBE unit can also separate any unreacted methanol into a separate stream for recycling into further reactions with isobutene. In one or more embodiments, the produced MTBE can exit the MTBE unit 104 via conduit 122. Separately, the butadiene-rich C$_4$ stream can exit the MTBE unit 104 via conduit 124.

The butadiene-rich C$_4$ stream exiting the MTBE unit 104 via conduit 124 is then transferred to the butadiene extraction unit (BD unit) 106. In the butadiene extraction unit 106, the butadiene-rich C$_4$ stream is reacted to extract the butadiene from the butadiene-rich C$_4$ stream. In one or more embodiments, butadiene is extracted from the C$_4$ stream by solvent extraction. In one or more embodiments, the butadiene extraction process can use N-methylpyrrolidone (NMP) as a selective solvent to recover butadiene from the C$_4$ stream. In at least one embodiment, dimethylformamide (DMF) can be used as a selective solvent for butadiene recovery. The butadiene extraction process results in a butenes-rich C$_4$ stream. In one or more embodiments, the extracted butadiene exits the extraction unit 106 via conduit 126. The butenes-rich C$_4$ stream exits the extraction unit 106 via conduit 128.

The butene-rich C$_4$ stream exiting the extraction unit 106 via conduit 128 is then fed to the isononanol unit 108. In the isononanol unit 108, at least a portion of the butenes-rich C$_4$ stream undergoes a series of reactions to produce an olefin-rich stream and an isononanol stream. Specifically, in one or more embodiments, the butenes of the butenes-rich C$_4$ stream undergo a dimerization reaction to form butene dimers (C$_8$ components). At least a portion of the butene dimers (C$_8$ components) can continue to react (oligomerize) to form further hydrocarbon oligomers, including C$_{12}$ and C$_{16}$ components. For example, butenes can undergo a dimerization reaction to form many products, such as n-octenes (2-octene, 3-octene, and 4-octene), methyl heptenes (3-ethyl-2-heptene, 3-methyl-3-heptene, and 6-methyl-1-heptene), and dimethyl hexenes (3,4-dimethyl-2-hexene and 3,4-dimethyl-3-hexene), as shown in reaction scheme (2).

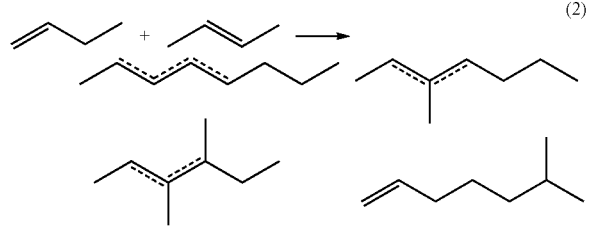

(2)

The isononanol process includes three primary steps: (1) hydroformylation of the iso-octene; (2) catalyst recovery and product demetalling; and (2) hydrogenation and purification of the product. In one or more embodiments, the formed isooctene in the isononanol unit 108 subsequently undergoes a hydroformylation reaction with syngas (comprising carbon monoxide and hydrogen) present in the isononanol unit 108 to form isononanal ("isononyl aldehyde"). An exemplary hydroformylation reaction of isooctene and syngas is shown below.

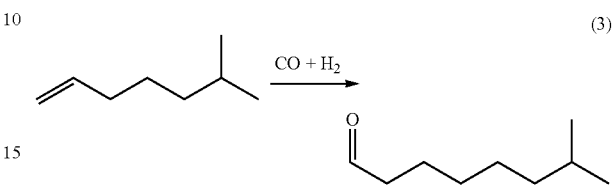

(3)

In one or more embodiments, the syngas can be produced in the furnace of the steam cracker 102 and can then be recovered in a cold box and recovery section of the steam cracker 102, for example. The produced syngas can then be transferred along with the C$_4$ stream to the MTBE unit 104, the extraction unit 106, and eventually to the isononanol unit 108. In at least one embodiment, the syngas present in the isononanol unit 108 can be from external sources (not shown) and can then be transferred to the isononanol unit 108. An exemplary hydroformylation may take place from 150° C. to 180° C., such as about 165° C., in the presence of a catalyst, such as a cobalt catalyst.

In embodiments, the catalyst may be recovered and the product of the hydroformylation may undergo demetalling. Various compressors, evaporators, and columns may be used to separate the catalyst from the product of the hydroformylation.

The formed isononanal undergoes a hydrogenation reaction with the hydrogen of the syngas present in the isononanol unit 108 to form isononanol. An exemplary hydrogenation may take place from 110° C. to 180° C., such as from 120° C. to 130° C. An exemplary hydrogenation reaction is shown in reaction scheme (4).

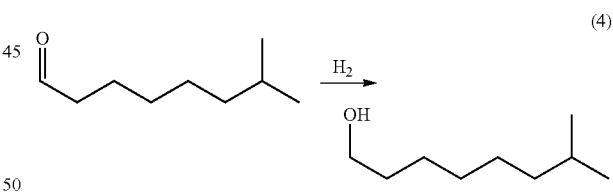

(4)

The formed isononanol exits the isononanol unit 108 via conduit 130 for collection and any further processing. The C$_8$, C$_{12}$, and C$_{16}$ components that remain from the dimerization and oligomerization reactions (collectively, the olefin-rich stream) exit the isononanol unit 108 via conduit 132. Any unreacted C$_4$ components, including butenes and/or butanes, can exit the isononanol unit 108 via conduit 134. In one or more embodiments, as shown in FIG. 1, the conduit 134 recycles the unreacted C$_4$ components back to the steam cracker 102.

In one or more embodiments, the unreacted C$_4$ components in the isononanol unit 108 include n-butenes and n-butanes. The formed C$_8$ components in the isononanol unit 108 can include 1-octene, n-octane, iso-octane, and n-nonanal. The formed C$_{12}$ components in the isononanol unit 108 can include isomers of dodecene, along with other C$_{12}$ olefins. The formed $C_{16}$ components in the isononanol unit 108 can include 1-hexadecene and 1-eicosene.

As shown in FIG. 2, the olefin-rich stream may be further processed in an olefin processing unit 110. In embodiments, the olefin processing unit 110 is an oxidation unit and the olefin-rich stream undergoes oxidation to produce epoxide gasoline blending components. In embodiments, the olefin processing unit 110 is a hydration unit and the olefin-rich stream undergoes hydration to produce alcohol gasoline blending components. In embodiments, the olefin processing unit 110 is a hydrogenation unit and the olefin-rich stream undergoes selective hydrogenation to produce paraffins. The epoxide gasoline blending components, alcohol gasoline blending components, or paraffins may exit the olefin processing unit through conduit 138.

Oxidation

Briefly, oxidation of olefins involves reacting the olefins with an oxidant in the presence of a catalyst composition. To perform the oxidation, an oxidant stream is added to the olefin processing unit 110, which in this embodiment is an oxidation unit, through conduit 142. Further, a catalyst stream may be added to the oxidation unit through conduit 144. The oxidation unit may include one or more types of oil refining equipment and apparatuses including, but not limited to, furnaces, compressors, reactors, gas-liquid separators, distillation units, heat exchangers, and pumps. Oxidation may occur in the gas phase or in the liquid phase. In embodiments, oxidation takes place in at least one reactor selected from the group consisting of a fixed-bed reactor, an ebullated-bed reactor, a moving bed reactor, a slurry bed reactor, and a combination of two or more thereof.

In embodiments using gas phase oxidation, the oxidant may be any appropriate oxidizing agent. For example, the oxidant used in gas phase oxidation may be selected from oxygen, air, nitrous oxide, and combinations of two or more of these.

In embodiments using gas phase oxidation, the catalyst composition used for the gas phase oxidation reaction may include copper oxide, zinc oxide, cerium oxide, aluminum oxide, and mixtures of two or more of these. For instance, the catalyst composition may include $Cu_xZ_{1-x}Al_2O_4$ where x ranges from 0 to 1. In embodiments, the catalyst composition used for the gas phase oxidation reaction includes from 20 weight percent (wt. %) to 45 wt. % copper oxide, from 12 wt. % to 20 wt. % zinc oxide, from 0.1 wt. % to 10 wt. % cerium oxide, and from 20 wt. % to 40 wt. % aluminum oxide. In embodiments, the catalyst composition used for the gas phase oxidation reaction may include highly dispersed zinc oxide, highly dispersed copper oxide, or a mixture of these two. In embodiments, the cerium oxide is in the form of particles having a diameter from 5 nm to 10 nm. In embodiments, the catalyst may exhibit an X-ray amorphous oxide phase.

In embodiments using gas phase oxidation, the oxidation may take place in a reactor with the reagents (i.e., oxidant and olefin-rich feed) and catalyst composition flowing through the reactor. In the gas phase oxidation reaction, the ratio of the volume of reagents flowing through the reactor to the volume of catalyst flowing through the reactor, or the gas hourly space velocity (GHSV), may be from 1,000 $h^{-1}$ to 20,000 $h^{-1}$, from 1,000 $h^{-1}$ to 15,000 $h^{-1}$, from 1,000 $h^{-1}$ to 10,000 $h^{-1}$, from 1,000 $h^{-1}$ to 5,000 $h^{-1}$, from 5,000 $h^{-1}$ to 20,000 $h^{-1}$, from 5,000 $h^{-1}$ to 15,000 $h^{-1}$, from 5,000 $h^{-1}$ to 10,000 $h^{-1}$, from 10,000 $h^{-1}$ to 20,000 $h^{-1}$, or even from 15,000 $h^{-1}$ to 20,000 $h^{-1}$.

In embodiments using gas phase oxidation, the oxidation may take place in a reactor at a pressure from 0.1 MPa to 3 MPa, from 0.1 MPa to 2.5 MPa, from 0.1 MPa to 2 MPa, from 0.1 MPa to 1.5 MPa, from 0.1 MPa to 1 MPa, from 0.1 MPa to 0.5 MPa, from 0.5 MPa to 3 MPa, from 1 MPa to 3 MPa, from 1.5 MPa to 3 MPa, from 2 MPa to 3 MPa, or even from 2.5 MPa to 3 MPa.

In embodiments using gas phase oxidation, the oxidation may take place in a reactor at a temperature from 200° C. to 600° C., from 200° C. to 550° C., from 200° C. to 500° C., from 200° C. to 450° C., from 200° C. to 400° C., from 200° C. to 250° C., from 250° C. to 600° C., from 250° C. to 550° C., from 300° C. to 500° C., from 300° C. to 600° C., from 350° C. to 600° C., from 400° C. to 600° C., from 450° C. to 600° C., from 500° C. to 600° C., or even from 550° C. to 600° C.

In the gas phase oxidation reaction, the ratio of the mass of reagents flowing through the reactor to the mass of catalyst flowing through the reactor, or the weight hourly space velocity (WHSV), may be from 1 $h^{-1}$ to 20 $h^{-1}$, from 1 $h^{-1}$ to 19 $h^{-1}$, from 1 $h^{-1}$ to 18 $h^{-1}$, from 1 $h^{-1}$ to 17 $h^{-1}$, from 1 $h^{-1}$ to 16 $h^{-1}$, from 1 $h^{-1}$ to 15 $h^{-1}$, from 1 $h^{-1}$ to 14 $h^{-1}$, from 1 $h^{-1}$ to 13 $h^{-1}$, from 1 $h^{-1}$ to 12 $h^{-1}$, from 1 $h^{-1}$ to 11 $h^{-1}$, from 1 $h^{-1}$ to 10 $h^{-1}$, from 1 $h^{-1}$ to 9 $h^{-1}$, from 1 $h^{-1}$ to 8 $h^{-1}$, from 1 $h^{-1}$ to 7 $h^{-1}$, from 1 $h^{-1}$ to 6 $h^{-1}$, from 1 $h^{-1}$ to 5 $h^{-1}$, from 1 $h^{-1}$ to 4 $h^{-1}$, from 1 $h^{-1}$ to 3 $h^{-1}$, from 1 $h^{-1}$ to 2 $h^{-1}$, from 2 $h^{-1}$ to 20 $h^{-1}$, from 3 $h^{-1}$ to 20 $h^{-1}$, from 4 $h^{-1}$ to 20 $h^{-1}$, from 5 $h^{-1}$ to 20 $h^{-1}$, from 5 $h^{-1}$ to 15 $h^{-1}$, from 6 $h^{-1}$ to 20 $h^{-1}$, from 7 $h^{-1}$ to 20 $h^{-1}$, from 8 $h^{-1}$ to 20 $h^{-1}$, from 8 $h^{-1}$ to 10 $h^{-1}$, from 9 $h^{-1}$ to 20 $h^{-1}$, from 10 $h^{-1}$ to 20 $h^{-1}$, from 11 $h^{-1}$ to 20 $h^{-1}$, from 12 $h^{-1}$ to 20 $h^{-1}$, from 13 $h^{-1}$ to 20 $h^{-1}$, from 14 $h^{-1}$ to 20 $h^{-1}$, from 15 $h^{-1}$ to 20 $h^{-1}$, from 16 $h^{-1}$ to 20 $h^{-1}$, from 17 $h^{-1}$ to 20 $h^{-1}$, from 18 $h^{-1}$ to 20 $h^{-1}$, or even from 19 $h^{-1}$ to 20 $h^{-1}$.

In embodiments using liquid phase oxidation, the oxidant may be selected from liquid oxidants consisting of one or more organic hydroperoxides, organic peroxides, and a combination of one or more organic hydroperoxides and organic peroxides. In embodiments, the oxidant used in liquid phase oxidation is selected from alkyl hydroperoxides, aryl-hydroperoxides, dialkyl peroxides, diaryl peroxides, peresters, hydrogen peroxide, and combinations of two or more of these.

In embodiments using liquid phase oxidation, the catalyst composition used for the liquid phase oxidation reaction may include an active transition metal, such as Mo(VI), W(VI), V(V), Ti(IV), and combinations of two or more of these. In embodiments, the catalyst composition may include a salt of the metal or organometallics. For example, the catalyst composition used for the liquid phase oxidation reaction may include sodium-tungstate. In embodiments, the transition metal catalyst exhibits Lewis acidity, and the oxidation potential of the transition metal catalyst is less than that of the oxidant. In embodiments, the catalyst composition comprises a salt of the active transition metal.

In embodiments using liquid phase oxidation, the liquid phase oxidation may take place in a reactor having an olefin-to-oxidant molar ratio from 1:1 to 1:50, from 1:5 to 1:50, from 1:10 to 1:50, from 1:15 to 1:50, from 1:20 to 1:50, from 1:25 to 1:50, from 1:30 to 1:50, from 1:35 to 1:50, from 1:40 to 1:50, from 1:45 to 1:50, from 1:1 to 1:45, from 1:1 to 1:40, from 1:1 to 1:35, from 1:1 to 1:30, from 1:1 to 1:25, from 1:1 to 1:20, from 1:1 to 1:15, from 1:1 to 1:10, or even from 1:1 to 1:5. In embodiments, the olefin-to-oxidant molar ratio is 1:1. In embodiments, the olefin-to-oxidant molar ratio is 1:5. In embodiments, the olefin-to-oxidant molar ratio is 1:50.

In embodiments using liquid phase oxidation, the oxidation may take place in a reactor at a pressure from 0.1 MPa to 3 MPa, from 0.1 MPa to 2.5 MPa, from 0.1 MPa to 2 MPa, from 0.1 MPa to 1.5 MPa, from 0.1 MPa to 1 MPa, from 0.1 MPa to 0.5 MPa, from 0.5 MPa to 3 MPa, from 1 MPa to 3 MPa, from 1.5 MPa to 3 MPa, from 2 MPa to 3 MPa, or even from 2.5 MPa to 3 MPa.

In embodiments using gas phase oxidation, the oxidation may take place in a reactor at a temperature from 20° C. to 100° C., from 20° C. to 90° C., from 20° C. to 80° C., from 20° C. to 70° C., from 20° C. to 60° C., from 20° C. to 50° C., from 20° C. to 40° C., from 20° C. to 30° C., from 30° C. to 100° C., from 40° C. to 100° C., from 50° C. to 100° C., from 60° C. to 100° C., from 70° C. to 100° C., from 80° C. to 100° C., or even from 90° C. to 100° C.

In the liquid phase oxidation reaction, the ratio of the mass of reagents flowing through the reactor to the mass of catalyst flowing through the reactor, or the weight hourly space velocity (WHSV), may be from 1 $h^{-1}$ to 20 $h^{-1}$, from 1 $h^{-1}$ to 19 $h^{-1}$, from 1 $h^{-1}$ to 18 $h^{-1}$, from 1 $h^{-1}$ to 17 $h^{-1}$, from 1 $h^{-1}$ to 16 $h^{-1}$, 1 $h^{-1}$ to 15 $h^{-1}$, from 1 $h^{-1}$ to 14 $h^{-1}$, from 1 $h^{-1}$ to 13 $h^{-1}$, from 1 $h^{-1}$ to 12 $h^{-1}$, from 1 $h^{-1}$ to 11 $h^{-1}$, from 1 $h^{-1}$ to 10 $h^{-1}$, from 1 $h^{-1}$ to 9 $h^{-1}$, from 1 $h^{-1}$ to 8 $h^{-1}$, from 1 $h^{-1}$ to 7 $h^{-1}$, from 1 $h^{-1}$ to 6 $h^{-1}$, 1 $h^{-1}$ to 5 $h^{-1}$, from 1 $h^{-1}$ to 4 $h^{-1}$, from 1 $h^{-1}$ to 3 $h^{-1}$, from 1 $h^{-1}$ to 2 $h^{-1}$, from 2 $h^{-1}$ to 20 $h^{-1}$, from 3 $h^{-1}$ to 20 $h^{-1}$, from 4 $h^{-1}$ to 20 $h^{-1}$, from 5 $h^{-1}$ to 20 $h^{-1}$, from 5 $h^{-1}$ to 15 $h^{-1}$, from 6 $h^{-1}$ to 20 $h^{-1}$, from 7 $h^{-1}$ to 20 $h^{-1}$, from 8 $h^{-1}$ to 20 $h^{-1}$, from 8 $h^{-1}$ to 10 $h^{-1}$, from 9 $h^{-1}$ to 20 $h^{-1}$, from 10 $h^{-1}$ to 20 $h^{-1}$, from 11 $h^{-1}$ to 20 $h^{-1}$, from 12 $h^{-1}$ to 20 $h^{-1}$, from 13 $h^{-1}$ to 20 $h^{-1}$, from 14 $h^{-1}$ to 20 $h^{-1}$, from 15 $h^{-1}$ to 20 $h^{-1}$, from 16 $h^{-1}$ to 20 $h^{-1}$, from 17 $h^{-1}$ to 20 $h^{-1}$, from 18 $h^{-1}$ to 20 $h^{-1}$, or even from 19 $h^{-1}$ to 20 $h^{-1}$.

Regardless of the type of oxidation, i.e., gas phase or liquid phase, the products of the oxidation include $C_8$, $C_{12}$, and $C_{16}$ epoxides. Because epoxides possess higher octane and cetane numbers than the corresponding olefins, the system produces high quality gasoline and diesel streams. In embodiments, the $C_8$, $C_{12}$, and $C_{16}$ epoxides may be separated from one another and added to gasoline ($C_8$) or diesel ($C_{12}$, $C_{16}$, or both $C_{12}$ and $C_{16}$) as blending components. Table 1 provides a comparison of the octane numbers of the $C_8$ components of the olefin-rich stream and the octane numbers of the analogous oxidized $C_8$ components. Notably, the $C_8$ paraffins do not undergo oxidation, as shown by the relatively unchanged RON after the oxidation reaction. Table 2 provides a comparison of the cetane number of the $C_{12}$ and $C_{16}$ components of the olefin-rich stream and the cetane number of the analogous oxidized $C_{12}$ and $C_{16}$ components. As can be seen from Table 2, the cetane number of the paraffinic compounds does not change after the oxidation reaction, indicating that the paraffinic compounds do not undergo the oxidation, but the cetane number of the olefinic compounds increases significantly.

TABLE 1

Octane Numbers[1] of Components of Pre- and Post-Oxidation Streams

| Component | RON Pre-Oxidation | RON Post-Oxidation |
|---|---|---|
| $C_8$ Olefins (33 pure components) | 86.6 | 141 |
| $C_8$ Paraffins (36 pure components) | 72.6 | N/C[2] |
| $C_8$ Mix[3] (76 pure components) | 78.9 | >110 |

[1]Research Octane Number;
[2]N/C = no change;
[3]All isomers of paraffins or olefins with a carbon number of 8 (e.g., alkylated pentanes, alkylated hexanes, etc.)

TABLE 2

Cetane Numbers of Components of Pre- and Post-Oxidation Streams

| Component | Cetane Number Pre-Oxidation | Cetane Number Post-Oxidation |
|---|---|---|
| Dodecane ($C_{12}$) | 91 | N/C[1] |
| Dodecene | 76 | 92 |
| Hexadecane ($C_{16}$) | 104 | N/C |
| Hexadecene | 87 | 95 |

[1]N/C = no change

Based on the values from Tables 1 and 2, oxidation of the olefin-rich stream may increase the RON an average from 10 to 60, from 10 to 55, from 10 to 50, from 10 to 45, from 10 to 40, from 10 to 35, from 10 to 30, from 10 to 25, from 10 to 20, from 10 to 15, from 15 to 60, from 20 to 60, from 25 to 60, from 30 to 60, from 35 to 60, from 40 to 60, from 45 to 60, from 50 to 60, or even from 55 to 60. Further, oxidation of the olefin-rich stream may increase the cetane number an average from 5 to 20, from 5 to 19, from 5 to 18, from 5 to 17, from 5 to 16, from 5 to 15, from 5 to 14, from 5 to 13, from 5 to 12, from 5 to 11, from 5 to 10, from 5 to 9, 5 to 8, from 5 to 7, from 5 to 6, from 6 to 20, from 7 to 20, from 8 to 20, from 9 to 20, from 10 to 20, from 11 to 20, from 12 to 20, from 13 to 20, from 14 to 20, from 15 to 20, from 16 to 20, from 17 to 20, from 18 to 20, or even from 19 to 20.

Hydration

In embodiments, the olefin processing unit 110 is a hydration unit and the olefin-rich stream undergoes hydration to produce alcoholic gasoline blending components. Briefly, hydration of olefins involves reacting the olefins with water in the presence of a catalyst composition, resulting in alcohols. To perform the hydration, a water stream is added to the olefin processing unit 110, which in this embodiment is a hydration unit, through conduit 142. Further, a catalyst stream may be added to the hydration unit through conduit 144. The hydration unit may include one or more types of oil refining equipment and apparatuses including, but not limited to, furnaces, compressors, reactors, gas-liquid separators, distillation units, heat exchangers, and pumps. In embodiments in which a liquid acid is included, contactor reactors of the type used in liquid acid alkylation processes may be used. In embodiments, hydration takes place in at least one reactor selected from the group consisting of a fixed-bed reactor, an ebullated-bed reactor, a moving bed reactor, a slurry bed reactor, and a combination of two or more thereof.

In embodiments, the catalyst composition used for the hydration reaction may include soluble homogeneous compounds or solid heterogeneous compounds selected from resins and amorphous or structured metal oxides having Lewis or Brønsted acid sites. The metal oxides may be selected from IUPAC Groups, 4-10, 13, and 14, which correspond to Groups IIIA, IVA, IVB, VB, VI, VII, and VIIIB of the Periodic Table. Catalyst particles may range from 0.15 mm to 6.5 mm, or 0.0625 inch to 0.25 inch (1.6 mm to 6.4 mm), with a surface area from 30 $m^2$/g to 100 $m^2$/g and pore diameter from 200 Å to 300 Å.

Exemplary commercially available catalysts are representative of those which have been found to be suitable for use in the hydration reaction. The Dow Chemical Company's AMBERLYST 15 is a macroporous catalyst with an acceptable lifetime and conversion rate, and it also has a beneficial physical and osmotic pressure resistance. Similarly, AMBERLYST 70, which is also a macroporous catalyst, has been found to exhibit beneficial characteristics and also maintains stability at relatively high temperatures, i.e. 180° C. to 200° C. AMBERLYST 70 has been found to be well-suited for the production of isopropyl alcohol and secondary butyl alcohol. As used herein, the term "macroporous" refers to a material having a pore size larger than 50 mm. Further exemplary catalysts include TREVER|LYST CAT400 and TREVER|LYST CAT410 from Chemra GmbH of Trier, Germany, both of which exhibit thermal stability up to 190° C. and are physically very stable. TREVER|LYST CAT410 also has a long life due to its specific porosity and may be used in alkylation reactions or where $AlCl_3$ or $BF_3$ cannot be used. A dual-phase catalyst of the type disclosed in U.S. Pat. No. 8,558,036, the entire content of which is incorporated herein by reference, may also be used in the described process. The dual phase catalyst system comprises a water soluble acid catalyst selected from phosphor-tungstic acid hydrate and tungstosilicic acid hydrate and a solid acid catalyst that is insoluble in water, and is capable of hydrating the mixed olefins without the separation of the mixed olefins prior to their contact with the dual phase catalyst system. An advantage of the dual phase catalyst system is that it is capable of converting the mixed olefins into the mixed alcohols at a conversion rate that is greater than that of the water soluble acid catalyst or the solid acid catalyst.

In embodiments, the hydration may take place in a reactor at a pressure from 1 MPa to 10 MPa, from 1 MPa to 9 MPa, from 1 MPa to 8 MPa, from 1 MPa to 7 MPa, from 1 MPa to 6 MPa, from 1 MPa to 5 MPa, from 1 MPa to 4 MPa, from 1 MPa to 3 MPa, from 1 MPa to 2 MPa, from 2 MPa to 10 MPa, from 3 MPa to 10 MPa, from 3 MPa to 8 MPa, from 4 MPa to 10 MPa, from 5 MPa to 10 MPa, from 5 MPa to 7 MPa, from 6 MPa to 10 MPa, from 7 MPa to 10 MPa, from 8 MPa to 10 MPa, or even from 9 MPa to 10 MPa.

In embodiments, the hydration may take place in a reactor at a temperature from 25° C. to 300° C., from 25° C. to 275° C., from 25° C. to 250° C., from 25° C. to 225° C., from 25° C. to 200° C., from 25° C. to 175° C., from 25° C. to 150° C., from 25° C. to 125° C., from 25° C. to 100° C., from 25° C. to 75° C., from 25° C. to 50° C., from 50° C. to 300° C., from 75° C. to 300° C., from 100° C. to 300° C., from 100° C. to 250° C., from 125° C. to 300° C., from 130° C. to 200° C., from 150° C. to 300° C., from 175° C. to 300° C., from 200° C. to 300° C., from 225° C. to 300° C., from 250° C. to 300° C., or even from 275° C. to 300° C.

In embodiments, the hydration may take place in a reactor having a WHSV from $0.01\ h^{-1}$ to $10\ h^{-1}$, from $0.01\ h^{-1}$ to $9\ h^{-1}$, from $0.01\ h^{-1}$ to $8\ h^{-1}$, from $0.01\ h^{-1}$ to $7\ h^{-1}$, from $0.01\ h^{-1}$ to $6\ h^{-1}$, $0.01\ h^{-1}$ to $5\ h^{-1}$, from $0.01\ h^{-1}$ to $4\ h^{-1}$, from $0.01\ h^{-1}$ to $3\ h^{-1}$, from $0.01\ h^{-1}$ to $2\ h^{-1}$, from $0.01\ h^{-1}$ to $1\ h^{-1}$, from $0.01\ h^{-1}$ to $0.9\ h^{-1}$, from $0.01\ h^{-1}$ to $0.8\ h^{-1}$, from $0.01\ h^{-1}$ to $0.7\ h^{-1}$, from $0.01\ h^{-1}$ to $0.6\ h^{-1}$, $0.01\ h^{-1}$ to $0.5\ h^{-1}$, from $0.01\ h^{-1}$ to $0.4\ h^{-1}$, from $0.01\ h^{-1}$ to $0.3\ h^{-1}$, from $0.01\ h^{-1}$ to $0.2\ h^{-1}$, from $0.01\ h^{-1}$ to $0.1\ h^{-1}$, from $0.01\ h^{-1}$ to $0.05\ h^{-1}$, from $0.05\ h^{-1}$ to $10\ h^{-1}$, from $0.05\ h^{-1}$ to $5\ h^{-1}$, from $0.1\ h^{-1}$ to $10\ h^{-1}$, from $0.1\ h^{-1}$ to $1\ h^{-1}$, from $0.2\ h^{-1}$ to $10\ h^{-1}$, from $0.3\ h^{-1}$ to $10\ h^{-1}$, from $0.4\ h^{-1}$ to $10\ h^{-1}$, from $0.5\ h^{-1}$ to $10\ h^{-1}$, from $0.6\ h^{-1}$ to $10\ h^{-1}$, from $0.7\ h^{-1}$ to $10\ h^{-1}$, from $0.8\ h^{-1}$ to $10\ h^{-1}$, from $0.9\ h^{-1}$ to $10\ h^{-1}$, from $1\ h^{-1}$ to $10\ h^{-1}$, from $2\ h^{-1}$ to $10\ h^{-1}$, from $3\ h^{-1}$ to $10\ h^{-1}$, from $4\ h^{-1}$ to $10\ h^{-1}$, from $5\ h^{-1}$ to $10\ h^{-1}$, from $6\ h^{-1}$ to $10\ h^{-1}$, from $7\ h^{-1}$ to $10\ h^{-1}$, from $8\ h^{-1}$ to $10\ h^{-1}$, or even from $9\ h^{-1}$ to $10\ h^{-1}$.

In embodiments, the hydration may take place in a reactor having a water-to-olefin molar ratio from 1:1 to 5:1, from 1:1 to 4:1, from 1:1 to 3:1, from 1:1 to 2:1, from 2:1 to 5:1, from 3:1 to 5:1, or even from 4:1 to 5:1, from 1:35 to 1:50, from 1:40 to 1:50, from 1:45 to 1:50, from 1:1 to 1:45, from 1:1 to 1:40, from 1:1 to 1:35, from 1:1 to 1:30, from 1:1 to 1:25, from 1:1 to 1:20, from 1:1 to 1:15, from 1:1 to 1:10, or even from 1:1 to 1:5. In embodiments, the water-to-olefin molar ratio is 5:1. In embodiments, the water-to-olefin molar ratio is 2:1. In embodiments, the water-to-olefin molar ratio is 1:1.

The products of the hydration include $C_8$, $C_{12}$, and $C_{16}$ alcohols. The resulting alcoholic $C_8$ stream has a higher octane number than the olefinic $C_8$ stream. In contrast, the alcoholic $C_{12}$ and $C_{16}$ streams have a lower cetane number compared to the olefinic $C_{12}$ and $C_{16}$ streams. However, the alcoholic $C_{12}$ and $C_{16}$ streams still meet the most stringent specifications set for the diesel fraction, which is a cetane number of 40. In embodiments, the $C_8$, $C_{12}$, and $C_{16}$ alcohols may be separated from one another and added to gasoline ($C_8$) or diesel ($C_{12}$, $C_{16}$, or both $C_{12}$ and $C_{16}$) as blending components. Because alcohols possess high lubricity, both the gasoline and the diesel fractions provide lubricity to the gasoline blend, avoiding the high cost of lubricity additives. Table 3 provides a comparison of the octane numbers of the $C_8$ components of the olefin-rich stream and the octane numbers of the analogous hydrated $C_8$ components. Notably, the $C_8$ paraffins do not undergo hydration, as shown by the relatively unchanged RON after the hydration reaction. Table 4 provides a comparison of the cetane number of the $C_{12}$ and $C_{16}$ components of the olefin-rich stream and the cetane number of the analogous hydrated $C_{12}$ and $C_{16}$ components. As can be seen from Table 4, the cetane number of the paraffinic compounds does not change after the hydration reaction, but the cetane number of the olefinic compounds decreases.

TABLE 3

Octane Numbers[1] of Components of Pre- and Post-Hydration Streams

| Component | RON Pre-Hydration | RON Post-Hydration |
|---|---|---|
| $C_8$ Olefins (33 pure components) | 86.6 | >110 |
| $C_8$ Paraffins (36 pure components) | 72.6 | N/C[2] |
| $C_8$ Mix[3] (76 pure components) | 78.9 | >110 |

[1]Research Octane Number;
[2]N/C = no change;
[3]All isomers of paraffins or olefins with a carbon number of 8 (e.g., alkylated pentanes, alkylated hexanes, etc.)

TABLE 4

Cetane Numbers of Components of Pre- and Post-Hydration Streams

| Component | Cetane Number Pre-Hydration | Cetane Number Post-Hydration |
|---|---|---|
| Dodecane ($C_{12}$) | 91 | N/C[1] |
| Dodecene | 76 | 56 |
| Hexadecane ($C_{16}$) | 104 | N/C |
| Hexadecene | 87 | 72 |

[1]N/C = no change

Based on the values from Tables 3 and 4, hydration of the olefin-rich stream may increase the RON an average from 10 to 60, from 10 to 55, from 10 to 50, from 10 to 45, from 10 to 40, from 10 to 35, from 10 to 30, from 10 to 25, from 10 to 20, from 10 to 15, from 15 to 60, from 20 to 60, from 25 to 60, from 30 to 60, from 35 to 60, from 40 to 60, from 45 to 60, from 50 to 60, or even from 55 to 60. Further, hydration of the olefin-rich stream may decrease the cetane number an average from 10 to 30, from 10 to 29, from 10 to 28, from 10 to 27, from 10 to 26, from 10 to 25, from 10 to 24, from 10 to 23, from 10 to 22, from 10 to 21, from 10 to 20, from 10 to 19, 10 to 18, from 10 to 17, from 10 to 16, from 10 to 15, from 10 to 14, from 10 to 13, from 10 to 12, from 10 to 11, from 11 to 30, from 12 to 30, from 13 to 30, from 14 to 30, from 15 to 30, from 16 to 30, from 17 to 30, from 18 to 300, from 19 to 30, from 20 to 30, from 21 to 30, from 22 to 30, from 23 to 30, from 24 to 30, from 25 to 30, from 26 to 300, from 27 to 30, from 28 to 300, or even from 29 to 30.

Hydrogenation

In embodiments, the olefin processing unit 110 is a hydrogenation unit and the olefin-rich stream undergoes selective hydrogenation to produce corresponding paraffins, which can then be cracked to produce light olefins, such as ethylene. Briefly, hydrogenation of olefins involves reacting the olefins with hydrogen in the presence of a catalyst composition, resulting in paraffins. To perform the hydrogenation, a hydrogen stream is added to the olefin processing unit 110, which in this embodiment is a hydrogenation unit, through conduit 142. Further, a catalyst stream may be added to the hydrogenation unit through conduit 144. The hydrogenation unit may include one or more types of oil refining equipment and apparatuses including, but not limited to, furnaces, compressors, reactors, gas-liquid separators, distillation units, heat exchangers, and pumps. In embodiments, hydrogenation takes place in at least one reactor selected from the group consisting of a fixed-bed reactor, an ebullated-bed reactor, a moving bed reactor, a slurry bed reactor, and a combination of two or more thereof.

In embodiments, the catalyst composition used for the hydrogenation reaction may include an active phase metal on a support. Exemplary active phase metals include, but are not limited to, nickel, molybdenum, tungsten, platinum, palladium, rhodium, ruthenium, gold, and combinations of two or more of these. Exemplary supports include amorphous alumina, crystalline silica-alumina, alumina, silica, and a combination of two or more thereof.

In embodiments, the hydrogenation may take place in a reactor at a pressure from 2 MPa to 10 MPa, from 2 MPa to 9 MPa, from 2 MPa to 8 MPa, from 2 MPa to 7 MPa, from 2 MPa to 6 MPa, from 2 MPa to 5 MPa, from 2 MPa to 4 MPa, from 2 MPa to 3 MPa, from 3 MPa to 10 MPa, from 4 MPa to 10 MPa, from 5 MPa to 10 MPa, from 6 MPa to 10 MPa, from 7 MPa to 10 MPa, from 8 MPa to 10 MPa, or even from 9 MPa to 10 MPa.

In embodiments, the hydrogenation may take place in a reactor at a temperature from 200° C. to 400° C., from 200° C. to 350° C., from 200° C. to 300° C., from 200° C. to 250° C., from 250° C. to 400° C., from 300° C. to 400° C., or even from 350° C. to 400° C.

In embodiments, the hydrogenation may take place in a reactor having a liquid flow rate to the catalyst volume within the reactor, or the liquid hourly space velocity (LHSV), may be from $1\ h^{-1}$ to $8\ h^{-1}$, from $1\ h^{-1}$ to $7\ h^{-1}$, from $1\ h^{-1}$ to $6\ h^{-1}$, $1\ h^{-1}$ to $5\ h^{-1}$, from $1\ h^{-1}$ to $4\ h^{-1}$, from $1\ h^{-1}$ to $3\ h^{-1}$, from $1\ h^{-1}$ to $2\ h^{-1}$, from $2\ h^{-1}$ to $8\ h^{-1}$, from $3\ h^{-1}$ to $8\ h^{-1}$, from $4\ h^{-1}$ to $8\ h^{-1}$, from $5\ h^{-1}$ to $8\ h^{-1}$, from $6\ h^{-1}$ to $8\ h^{-1}$, or even from $7\ h^{-1}$ to $8\ h^{-1}$.

In embodiments, the hydrogenation may take place in a reactor having a hydrogen-to-olefin molar ratio from 100 L/L to 1000 L/L, from 100 L/L to 900 L/L, from 100 L/L to 800 L/L, from 100 L/L to 700 L/L, from 100 L/L to 600 L/L, from 100 L/L to 500 L/L, from 100 L/L to 400 L/L, from 100 L/L to 300 L/L, from 100 L/L to 200 L/L, from 200 L/L to 1000 L/L, from 300 L/L to 1000 L/L, from 400 L/L to 1000 L/L, from 500 L/L to 1000 L/L, from 600 L/L to 1000 L/L, from 700 L/L to 1000 L/L, from 800 L/L to 1000 L/L, or even from 900 L/L to 1000 L/L.

The products of the hydrogenation include $C_8$, $C_{12}$, and $C_{16}$ paraffins. The resulting paraffinic $C_8$ stream has a lower octane number than the olefinic $C_8$ stream. In contrast, the paraffinic $C_{12}$ and $C_{16}$ streams have a higher cetane number compared to the olefinic $C_{12}$ and $C_{16}$ streams. In embodiments, the $C_8$, $C_{12}$, and $C_{16}$ paraffinic streams may be cracked to produce light olefins, such as ethylene. In embodiments, the $C_8$, $C_{12}$, and $C_{16}$ paraffins may be separated from one another and added to gasoline ($C_8$) or diesel ($C_{12}$, $C_{16}$, or both $C_{12}$ and $C_{16}$) as blending components. Table 5 provides a comparison of the octane numbers of the $C_8$ components of the olefin-rich stream and the octane numbers of the analogous hydrogenated $C_8$ components. Notably, the $C_8$ paraffins do not undergo hydrogenation, as shown by the relatively unchanged RON after the hydrogenation reaction. Table 6 provides a comparison of the cetane numbers of the $C_{12}$ and $C_{16}$ components of the olefin-rich stream and the cetane numbers of the analogous hydrogenated $C_{12}$ and $C_{16}$ components. As can be seen from Table 6, the cetane number of the paraffinic compounds does not change after the hydrogenation reaction, but the cetane number of the olefinic compounds increases significantly.

TABLE 5

Octane Numbers[1] of Components of Pre- and Post-Hydrogenation Streams

| Component | RON Pre-Hydrogenation | RON Post-Hydrogenation |
|---|---|---|
| $C_8$ Olefins (33 pure components) | 86.6 | 72.6 |
| $C_8$ Paraffins (36 pure components) | 72.6 | N/C[2] |
| $C_8$ Mix[3] (76 pure components) | 78.9 | 72.6 |

[1]Research Octane Number;
[2]N/C = no change;
[3]All isomers of paraffins or olefins with a carbon number of 8 (e.g., alkylated pentanes, alkylated hexanes, etc.)

TABLE 6

Cetane Numbers of Components of Pre- and Post-Hydrogenation Streams

| Component | Cetane Number Pre-Hydrogenation | Cetane Number Post-Hydrogenation |
|---|---|---|
| Dodecane ($C_{12}$) | 91 | N/C[1] |
| Dodecene | 76 | 91 |
| Hexadecane ($C_{16}$) | 104 | N/C |
| Hexadecene | 87 | 102 |

[1]N/C = no change

Based on the values from Tables 5 and 6, hydrogenation of the olefin-rich stream may decrease the RON an average from 0 to 15, from 0 to 14, from 0 to 13, from 0 to 12, from 0 to 11, from 0 to 10, from 0 to 9, from 0 to 8, from 0 to 7, from 0 to 6, from 0 to 5, from 0 to 4, from 0 to 3, from 0 to 2, from 0 to 1, from 1 to 15, from 2 to 15, from 3 to 15, from 4 to 15, from 5 to 15, from 6 to 15, from 7 to 15, from 8 to 15, from 9 to 15, from 10 to 15, from 11 to 15, from 12 to 15, from 13 to 15, or even from 14 to 15. Further, hydrogenation of the olefin-rich stream may increase the cetane number an average from 0 to 15, from 0 to 14, from 0 to 13, from 0 to 12, from 0 to 11, from 0 to 10, from 0 to 9, from 0 to 8, from 0 to 7, from 0 to 6, from 0 to 5, from 0 to 4, from 0 to 3, from 0 to 2, from 0 to 1, from 1 to 15, from 2 to 15, from 3 to 15, from 4 to 15, from 5 to 15, from 6 to 15, from 7 to 15, from 8 to 15, from 9 to 15, from 10 to 15, from 11 to 15, from 12 to 15, from 13 to 15, or even from 14 to 15.

According to a first aspect, either alone or in combination with any other aspect, a method for producing alcohol gasoline blending components includes cracking, in a steam cracker, a hydrocarbon feed to form a first ethylene stream, a first propylene stream, and a $C_4$ stream comprising isobutene and butadiene; reacting, in a methyl tertiary butyl ether (MTBE) unit, the $C_4$ stream with a methanol stream to form MTBE and a butadiene-rich $C_4$ stream; selectively hydrogenating, in a butadiene unit, the butadiene-rich $C_4$ stream to form a butene-rich $C_4$ stream including butene-1, cis-butene-2, and trans-butene-2; producing, in an isononanol unit, isononanol and an olefin-rich stream from the butene-rich $C_4$ stream; and hydrating the olefin-rich stream in a hydration unit by combining the olefin-rich stream with a water stream and a catalyst composition to produce the alcohol gasoline blending components.

According to a second aspect, either alone or in combination with any other aspect, the alcohol gasoline blending components comprise $C_8$-alcohols, $C_{12}$-alcohols, and $C_{16}$-alcohols.

According to a third aspect, either alone or in combination with any other aspect, the hydration unit comprises at least one reactor selected from the group consisting of a fixed-bed reactor, an ebullated-bed reactor, a moving bed reactor, a slurry bed reactor, and a combination of two or more thereof.

According to a fourth aspect, either alone or in combination with any other aspect, the catalyst composition comprises a soluble homogeneous or heterogeneous catalyst comprising a resin, an amorphous oxide of a metal, a structured oxide of a metal, or a combination of two or more thereof.

According to a fifth aspect, either alone or in combination with any other aspect, the soluble homogenous or heterogeneous catalyst comprises Lewis acid sites, Brønsted acid sites, or a combination of Lewis acid sites and Brønsted acid sites.

According to a sixth aspect, either alone or in combination with any other aspect, the metal is selected from IUPAC Groups 4-10, 13, and 14 of the periodic table of elements.

According to a seventh aspect, either alone or in combination with any other aspect, the soluble homogenous or heterogeneous catalyst comprises one or more dual-phase catalyst comprising a water-soluble acid catalyst and a water-insoluble acid catalyst.

According to an eighth aspect, either alone or in combination with any other aspect, the water-soluble acid catalyst is selected from the group consisting of phosphor-tungstic acid hydrate, tungsto-silicic acid hydrate, and combination thereof.

According to a ninth aspect, either alone or in combination with any other aspect, the soluble homogenous or heterogeneous catalyst exhibits thermal stability at 180° C. to 200° C.

According to a tenth aspect, either alone or in combination with any other aspect, at least a portion of the hydration unit has a water-to-olefin ratio from 1:1 to 5:1.

According to an eleventh aspect, either alone or in combination with any other aspect, at least a portion of the hydration unit has a water-to-olefin ratio of about 1:1.

According to a twelfth aspect, either alone or in combination with any other aspect, at least a portion of the hydration unit has a pressure from 1 MPa to 10 MPa.

According to a thirteenth aspect, either alone or in combination with any other aspect, at least a portion of the hydration unit has a pressure from 5 MPa to 7 MPa.

According to a fourteenth aspect, either alone or in combination with any other aspect, at least a portion of the hydration unit has a temperature from 25° C. to 300° C.

According to a fifteenth aspect, either alone or in combination with any other aspect, at least a portion of the hydration unit has a temperature from 130° C. to 200° C.

According to a sixteenth aspect, either alone or in combination with any other aspect, at least a portion of the hydration unit has a weight hourly space velocity from 0.01 $h^{-1}$ to 10 $h^{-1}$.

According to a seventeenth aspect, either alone or in combination with any other aspect, at least a portion of the hydration unit has a gas hourly space velocity from 0.1 $h^{-1}$ to 1 $h^{-1}$.

According to an eighteenth aspect, either alone or in combination with any other aspect, the method further includes separating the $C_8$-alcohols, the $C_{12}$-alcohols, and the $C_{16}$-alcohols from one another to produce a $C_8$-alcohol rich stream and a $C_{12}$- and $C_{16}$-alcohol rich stream; blending at least a portion of the $C_8$-alcohol rich stream with gasoline; and blending at least a portion of the $C_{12}$- and $C_{16}$-alcohol rich stream with diesel.

EXAMPLES

Using embodiments described above, an exemplary scheme for producing isononanol and gasoline and diesel blending components was performed.

Synthesis of Isononanol and Recovery of Hydroformylation Catalyst

Isooctene and syngas react at 165° C. in the presence of a cobalt catalyst in a series of 3 hydroformylation reactors. Recycle compressors are provided to facilitate mass transfer. The crude product, along with recycle streams from the preformer, the evaporator, and the demetalling column (described below), are sent to a stripper column. Volatile $HCo(CO)_4$ is stripped overhead and is then absorbed by a chilled stream of makeup isooctene in the absorber, from which the bottoms are sent to the hydroformylation reactors. Bottoms from the stripping column are separated into organic and aqueous streams. The organic stream is extracted off acid in the wash column and is then split into a net product stream and a recycle stream. The recycle stream is used in the demetalling column. The aqueous stream from the decanter, along with that from the wash column, are sent to the demetalling column for removal of trace Co by extraction using the organic recycle from the wash column. The evaporator bottoms, along with an organic recycle stream and a syngas stream, are pumped to a preformer, which operates at 120° C. and 207.5 bar (20.75 MPa). The performer effluent is sent to the stripping column described above. Decobalted hydroformylation product and a small amount of water are pumped to multi-tube hydrogenation reactors. Hydrogenation is conducted at 200° C. and 70 bar (7 MPa). The liquid effluent is flashed and distilled in two columns to remove light ends and heavy ends. It is further hydrogenated in the hydrofinisher at 130° C. and 55 bar (5.5 MPa) to minimize carbonyls. The crude isononanol (from the hydrogenation) is refined utilizing three distillation columns. From the first column the light ends stream (fractioned at the top of the column) can be recycled to the hydroformylation stage. From the second column, the unconverted aldehyde (in a small amount of alcohol) stream is recycled to the hydrogenation stage. From the third column, the refined isononanol can be sent to storage or to a hydrorefiner while the heavy ends stream (bottoms olefin-rich stream) can be further treated.

Example 1: Oxidation

A 1000 kiloton per annum (KTA) mixed $C_4$ feed from the steam cracker of the system shown in FIG. 1 is used downstream in the subsequent units of the system shown in FIG. 1, ultimately resulting in an isononanol stream and an olefin-rich stream. The olefin-rich stream is allowed to pass into an oxidation unit. Molybdenum acetylacetonate (2.5× $10^{-5}$ moles) is used as the catalyst, and this catalyst is pre-dissolved in the hydrocarbon feed. The oxidant used is t-butylhydroperoxides added in a molar ratio of 1:1 olefin-to-oxidant. The oxidation unit is operated at 85° C. and 0.1 MPa of pressure, with a LHSV of 1 $h^{-1}$. The material balance in KTA for this process is provided in Table 7, in which conduit numbers correspond to the conduits described above as to FIG. 1 and FIG. 2.

TABLE 7

Material Balance Using Oxidation

| | Conduit (feed stream KTA) | | | | | | | | |
|---|---|---|---|---|---|---|---|---|---|
| | 118 | 120 | 122 | 124 | 126 | 128 | 130 | 134 | 138 |
| $H_2$ | 0 | 0 | 0 | 0 | 0 | 0 | 0 | 0 | 0 |
| MeOH | 0 | 125 | 0 | 0 | 0 | 0 | 0 | 0 | 0 |
| MTBE | 0 | 0 | 344 | 0 | 0 | 0 | 0 | 0 | 0 |
| 1,3-butadiene | 410 | 0 | 0 | 410 | 410 | 0 | 0 | 0 | 0 |
| iso-butene | 220 | 0 | 0 | 0 | 0 | 0 | 0 | 0 | 0 |
| cis-2-butene | 80 | 0 | 0 | 80 | 0 | 80 | 0 | 13 | 0 |
| trans-2-butene | 70 | 0 | 0 | 70 | 0 | 70 | 0 | 12 | 0 |
| 1-butene | 110 | 0 | 0 | 110 | 0 | 110 | 0 | 41 | 0 |
| iso-butane | 40 | 0 | 0 | 40 | 0 | 40 | 0 | 47 | 0 |
| n-butane | 70 | 0 | 0 | 70 | 0 | 70 | 0 | 81 | 0 |
| Isononanol | 0 | 0 | 0 | 0 | 0 | 0 | 158 | 0 | 0 |
| $C_8$ | 0 | 0 | 0 | 0 | 0 | 0 | 0 | 0 | 10 |
| $C_{12}$ | 0 | 0 | 0 | 0 | 0 | 0 | 0 | 0 | 23 |
| $C_{16}$ | 0 | 0 | 0 | 0 | 0 | 0 | 0 | 0 | 8 |
| Total | 1000 | 125 | 344 | 780 | 410 | 370 | 158 | 193 | 42 |

Example 2: Hydration

A 100 kiloton per annum (KTA) mixed $C_4$ feed from the steam cracker of the system shown in FIG. 1 is used downstream in the subsequent units of the system shown in FIG. 1, ultimately resulting in an isononanol stream and an olefin-rich stream. The olefin-rich stream is allowed to pass into a water hydration unit. A resin catalyst, AMBERLITE® 15 is used as the catalyst. The water is added in a molar ratio of 1:1 olefin-to-water. The hydration unit is operated at 180° C. and 3 MPa of pressure, with a LHSV of 1 $h^{-1}$. The material balance in KTA for this process is provided in Table 8, in which conduit numbers correspond to the conduits described above as to FIG. 1 and FIG. 2.

TABLE 8

Material Balance Using Hydration

| | Conduit (feed stream KTA) | | | | | | | | |
|---|---|---|---|---|---|---|---|---|---|
| | 118 | 120 | 122 | 124 | 126 | 128 | 130 | 134 | 138 |
| $H_2$ | 0 | 0 | 0 | 0 | 0 | 0 | 0 | 0 | 0 |
| MeOH | 0 | 125 | 0 | 0 | 0 | 0 | 0 | 0 | 0 |
| MTBE | 0 | 0 | 344 | 0 | 0 | 0 | 0 | 0 | 0 |
| 1,3-butadiene | 410 | 0 | 0 | 410 | 410 | 0 | 0 | 0 | 0 |
| iso-butene | 220 | 0 | 0 | 0 | 0 | 0 | 0 | 0 | 0 |
| cis-2-butene | 80 | 0 | 0 | 80 | 0 | 80 | 0 | 13 | 0 |
| trans-2-butene | 70 | 0 | 0 | 70 | 0 | 70 | 0 | 12 | 0 |
| 1-butene | 110 | 0 | 0 | 110 | 0 | 110 | 0 | 41 | 0 |
| iso-butane | 40 | 0 | 0 | 40 | 0 | 40 | 0 | 47 | 0 |
| n-butane | 70 | 0 | 0 | 70 | 0 | 70 | 0 | 81 | 0 |
| Isononanol | 0 | 0 | 0 | 0 | 0 | 0 | 158 | 0 | 0 |
| $C_8$ | 0 | 0 | 0 | 0 | 0 | 0 | 0 | 0 | 11 |
| $C_{12}$ | 0 | 0 | 0 | 0 | 0 | 0 | 0 | 0 | 25 |
| $C_{16}$ | 0 | 0 | 0 | 0 | 0 | 0 | 0 | 0 | 9 |
| Total | 1000 | 125 | 344 | 780 | 410 | 370 | 158 | 193 | 45 |

Example 3: Selective Hydrogenation

A 1000 kiloton per annum (KTA) mixed $C_4$ feed from the steam cracker of the system shown in FIG. 1 is used downstream in the subsequent units of the system shown in FIG. 1, ultimately resulting in an isononanol stream and an olefin-rich stream. The olefin-rich stream is allowed to pass into a hydrogenation unit. A hydrogenation catalyst containing platinum as an active phase metal on a support containing USY zeolite and alumina is used as the catalyst. The hydrogen is added at 100 SLt/Lt hydrogen-to-oil. The hydrogenation unit is operated at 180° C. and 6 MPa of pressure, with a LHSV of 1 $h^{-1}$. The material balance in KTA for this process is provided in Table 9, in which conduit numbers correspond to the conduits described above as to FIG. 1 and FIG. 2.

TABLE 9

Material Balance Using Selective Hydrogenation

| | Conduit (feed stream KTA) | | | | | | | | |
|---|---|---|---|---|---|---|---|---|---|
| | 118 | 120 | 122 | 124 | 126 | 128 | 130 | 134 | 138 |
| $H_2$ | 0 | 0 | 0 | 0 | 0 | 0 | 0 | 0 | 0 |
| MeOH | 0 | 125 | 0 | 0 | 0 | 0 | 0 | 0 | 0 |
| MTBE | 0 | 0 | 344 | 0 | 0 | 0 | 0 | 0 | 0 |
| 1,3-butadiene | 410 | 0 | 0 | 410 | 410 | 0 | 0 | 0 | 0 |
| iso-butene | 220 | 0 | 0 | 0 | 0 | 0 | 0 | 0 | 0 |
| cis-2-butene | 80 | 0 | 0 | 80 | 0 | 80 | 0 | 13 | 0 |
| trans-2-butene | 70 | 0 | 0 | 70 | 0 | 70 | 0 | 12 | 0 |
| 1-butene | 110 | 0 | 0 | 110 | 0 | 110 | 0 | 41 | 0 |
| iso-butane | 40 | 0 | 0 | 40 | 0 | 40 | 0 | 47 | 0 |
| n-butane | 70 | 0 | 0 | 70 | 0 | 70 | 0 | 81 | 0 |
| Isononanol | 0 | 0 | 0 | 0 | 0 | 0 | 158 | 0 | 0 |
| $C_8$ | 0 | 0 | 0 | 0 | 0 | 0 | 0 | 0 | 10 |
| $C_{12}$ | 0 | 0 | 0 | 0 | 0 | 0 | 0 | 0 | 23 |
| $C_{16}$ | 0 | 0 | 0 | 0 | 0 | 0 | 0 | 0 | 8 |
| Total | 1000 | 125 | 344 | 780 | 410 | 370 | 158 | 193 | 42 |

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient"

denotes an existing physical condition of the component and, as such, is to be taken as a definite recitation of the structural characteristics of the component.

The singular forms "a," "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used in this disclosure and in the appended claims, the words "comprise," "has," and "include" and all grammatical variations thereof are each intended to have an open, non-limiting meaning that does not exclude additional elements or steps.

As used in this disclosure, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

What is claimed is:

1. A method for producing alcohol gasoline blending components, the method comprising:
   cracking, in a steam cracker, a hydrocarbon feed to form a first ethylene stream, a first propylene stream, and a $C_4$ stream comprising isobutene and butadiene;
   reacting, in a methyl tertiary butyl ether (MTBE) unit, the $C_4$ stream with a methanol stream to form MTBE and a butadiene-rich $C_4$ stream;
   selectively hydrogenating, in a butadiene unit, the butadiene-rich $C_4$ stream to form a butene-rich $C_4$ stream including butene-1, cis-butene-2, and trans-butene-2;
   producing, in an isononanol unit, isononanol and an olefin-rich stream from the butene-rich $C_4$ stream; and
   hydrating the olefin-rich stream in a hydration unit by combining the olefin-rich stream with a water stream and a catalyst composition to produce the alcohol gasoline blending components.

2. The method of claim 1, wherein the alcohol gasoline blending components comprise $C_8$-alcohols, $C_{12}$-alcohols, and $C_{16}$-alcohols.

3. The method of claim 1, wherein the catalyst composition comprises a soluble homogeneous or heterogeneous catalyst comprising a resin, an amorphous oxide of a metal, a structured oxide of a metal, or a combination of two or more thereof.

4. The method of claim 3, wherein the soluble homogenous or heterogeneous catalyst comprises Lewis acid sites, Brønsted acid sites, or a combination of Lewis acid sites and Brønsted acid sites.

5. The method of claim 3, wherein the metal is selected from IUPAC Groups 4-10, 13, and 14 of the periodic table of elements.

6. The method of claim 3, wherein the soluble homogenous or heterogeneous catalyst comprises one or more dual-phase catalyst comprising a water-soluble acid catalyst and a water-insoluble acid catalyst.

7. The method of claim 6, wherein the water-soluble acid catalyst is selected from the group consisting of phosphortungstic acid hydrate, tungsto-silicic acid hydrate, and combination thereof.

8. The method of claim 3, wherein the soluble homogenous or heterogeneous catalyst exhibits thermal stability at 180° C. to 200° C.

9. The method of claim 1, wherein at least a portion of the hydration unit has a water-to-olefin ratio from 1:1 to 5:1.

10. The method of claim 1, wherein at least a portion of the hydration unit has a pressure from 1 MPa to 10 MPa.

11. The method of claim 1, wherein at least a portion of the hydration unit has a temperature from 25° C. to 300° C.

12. The method of claim 1, wherein at least a portion of the hydration unit has a temperature from 130° C. to 200° C.

13. The method of claim 1, wherein at least a portion of the hydration unit has a weight hourly space velocity from 0.01 $h^{-1}$ to 10 $h^{-1}$.

14. The method of claim 1, wherein at least a portion of the hydration unit has a gas hourly space velocity from 0.1 $h^{-1}$ to 1 $h^{-1}$.

15. The method of claim 2, further comprising:
   separating the $C_8$-alcohols, the $C_{12}$-alcohols, and the $C_{16}$-alcohols from one another to produce a $C_8$-alcohol rich stream and a $C_{12}$- and $C_{16}$-alcohol rich stream;
   blending at least a portion of the $C_8$-alcohol rich stream with gasoline; and
   blending at least a portion of the $C_{12}$- and $C_{16}$-alcohol rich stream with diesel.

* * * * *